United States Patent [19]

Nolte et al.

[11] Patent Number: 5,085,074
[45] Date of Patent: Feb. 4, 1992

[54] TEST DEVICE FOR DETERMINING ADHESIVE STRENGTH OF LACQUER ON A TUBE

[75] Inventors: Roger Nolte, Cologne; Herbert Röhrig, Berg-Gladbach; Franz-Josef Roth, Cologne, all of Fed. Rep. of Germany

[73] Assignee: Madaus AG, Cologne, Fed. Rep. of Germany

[21] Appl. No.: 669,882

[22] Filed: Mar. 14, 1991

[30] Foreign Application Priority Data

Mar. 21, 1990 [DE] Fed. Rep. of Germany ....... 4009081

[51] Int. Cl.⁵ ............................................... G01N 3/32
[52] U.S. Cl. .................................... 73/150 A; 73/797
[58] Field of Search ...................... 73/150 A, 790, 796, 73/827, 837, 797, 799

[56] References Cited

U.S. PATENT DOCUMENTS

| 2,533,076 | 12/1950 | Williams | 73/150 A |
|---|---|---|---|
| 2,669,863 | 2/1954 | Schneider | 73/796 X |
| 3,354,704 | 11/1967 | Gloor | 73/796 |
| 3,580,065 | 5/1971 | Strittmater et al. | 73/150 A |
| 3,714,821 | 2/1973 | Gilley | 73/797 X |
| 4,009,606 | 3/1977 | Clebant et al. | 73/797 |
| 4,586,371 | 5/1986 | Ivie et al. | 73/150 A |
| 4,957,004 | 9/1990 | McKinlay et al. | 73/150 A X |

FOREIGN PATENT DOCUMENTS 195231 8/1990 Japan ....................................... 73/827

Primary Examiner—Allan N. Shoap
Assistant Examiner—G. Bradley Bennett
Attorney, Agent, or Firm—Felfe & Lynch

[57] ABSTRACT

The device includes a base plate with a recessed seating for the shoulder of a tube with a threaded neck and a compressing mechanism engaging the open end of the tube body, the compressing mechanism being mounted axially with respect to the tube. The compressing mechanism is a reciprocable rod (20) which, on the end thereof facing the base plate (26), has a clamping head (30) for clamping the open end of the tube body. In a conical recess in the base plate (26), there is provided an internally threaded bore for screwing in the threaded neck of the tube (1).

9 Claims, 4 Drawing Sheets

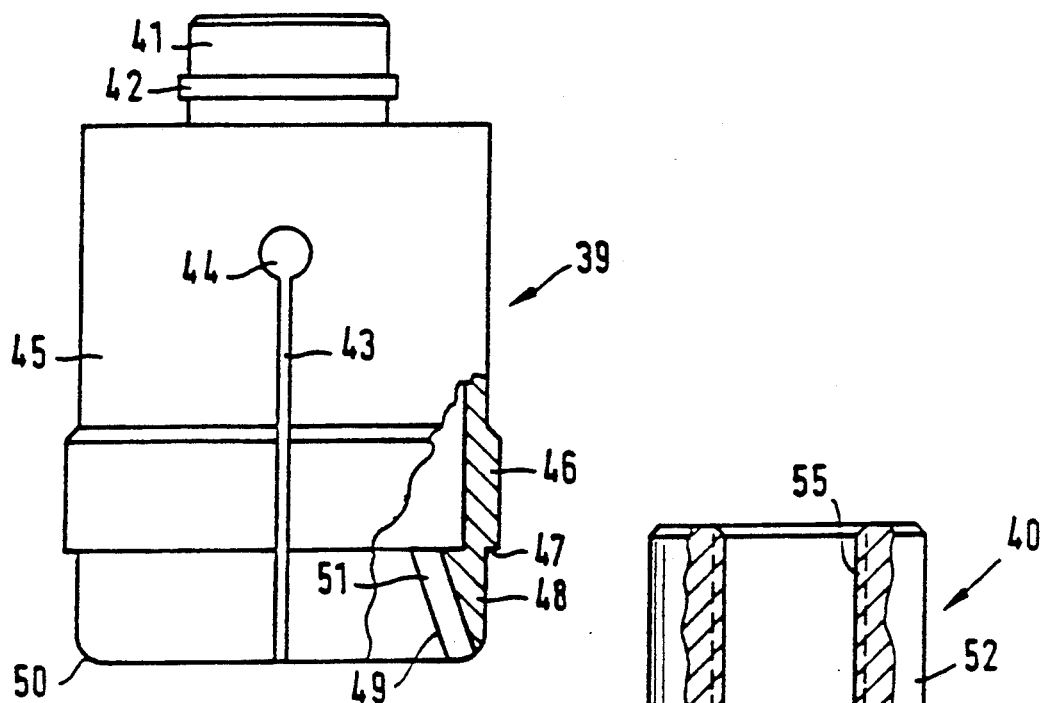
FIG. 4
FIG. 6
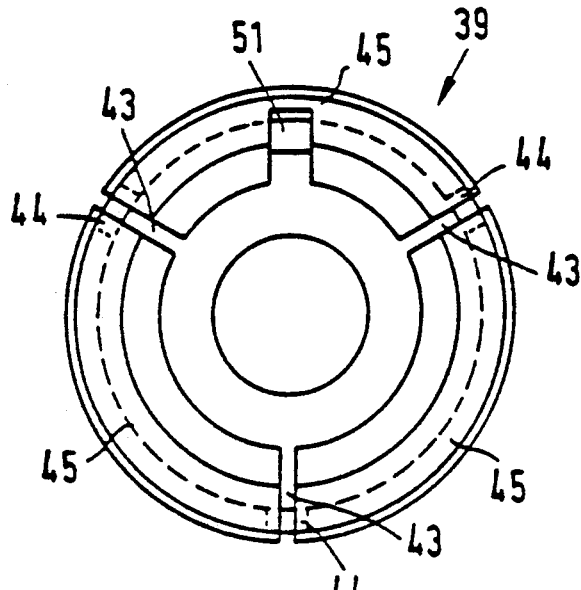
FIG. 5

TEST DEVICE FOR DETERMINING ADHESIVE STRENGTH OF LACQUER ON A TUBE

BACKGROUND OF THE INVENTION

The present invention is concerned with a test device for the determination of the strength of adhesion of a protective lacquering on the body of a collapsable tube, which device comprises a base plate with a recessed seating for the shoulder of a tube with threaded neck and a compressing mechanism engaging the upper open end of the tube body, the compressing mechanism being movable against the base plate.

Cylindrical and conical tubes made of aluminium are provided internally and externally with a protective lacquering which must have a high adhesive strength in order that it does not tear or loosen from the aluminium in the case of deformation by squeezing or rolling up in the course of emptying the tube since, in the case of the internal protective lacquering, this would result in an impairment of the contents of the tube.

For testing the protective lacquering, hitherto a test device has been used which has a guide column. The inventive test device includes a passage of a guide mandrel which is loosely placed in the interior of the tube. The tube casing is manually pressed together concertina-like by pressure which is as uniform as possible with a predetermined rate of compression of 100 to 400 mm/s of the tube body. The compressed tube body is then removed from the test device and manually pulled out in the axial direction. The compression edges of the pulled-out tube are investigated visually for crack formation or for loosening of the internal and external protective lacquering. In the case of this manually operated compression device, the maintenance of the predetermined rate of compression is difficult and, in the case of a series of tubes to be tested, can practically not be reproduced. Furthermore, the manual pulling out of the compressed tubes is laborious and requires a great amount of strength. Since twisting and bending of the tube body can thereby not be excluded, such accidental additional stresses can falsify the results of the test.

SUMMARY OF THE INVENTION

It is an object of the present invention to provide a test device which automatically provides dependable test results which are always. reproducible. The inventive test device includes a base plate with a recessed seating for the shoulder of a tube with a threaded neck and a compressing mechanism engaging the open end of the tube body, the compressing mechanism being mounted axially with respect to said tube. The compressing mechanism is a reciprocable rod (20) which, on the end thereof facing the base plate (26), has a clamping head (30) for clamping the open end of the tube body. In a conical recess in the base plate (26), there is provided an internally threaded bore for screwing in the threaded neck of the tube (1).

The test device according to the present invention operates at a predetermined uniform rate of compression which, in particular, can be 157 mm/s and, at the same rate, the concertina-like compressed tube body, clamped on its ends, is also pulled out in the axial direction. With a high degree of dependability, each tube can be compressed concertina-like to 15±5% of the length of the tube body, the compression and pulling out rates thereby being the same in all tests. Due to the absence of any kind of manual handling, the results obtained can be reproduced at any time. Each linearly pulled out tube body is cut axially and laid out flat so that there is obtained a creased strip of material, readily viewable on both sides, for visual examination.

According to an advantageous embodiment of the present invention, the rod is mounted in a guide of a yoke stanchion and driven via an external toothed rod member by a driving element coupled with an electromotor, the rod having a contact member which cooperates with limit switches arranged according to height. The yoke stanchion is arranged upright and the guide is Preferably present on the end of its substantially horizontal upper arm. For coupling the toothed wheel serving as driving element with the electromotor, there is used a toothed belt which runs outside of the yoke stanchion around belt pulleys. The limit switches arranged according to height on a bar attached vertically to the yoke stanchion serve for the adjustment of the compression path depending upon the particular length of the tube body.

The yoke stanchion and the electromotor are advantageously housed in a casing made of transparent material which, in the region of the base plate and of the clamping head, has a casing opening closed by a hinged flap through which the tube can be fixed in the test device or removed therefrom. The functioning of the test device can be observed through the transparent casing. In rapid succession, a plurality of tubes can be compressed and pulled out with the same speed of working so that, by means of accelerated quality control, a comparatively large portion of a tube production can be tested and the general level of quality can be increased. Via an operating element, the hinged flap activates a motor safety switch which makes possible a starting of the motor only when the hinged flap is closed. The electromotor can be controlled by means of an electric control device positioned outside of the casing.

In the rod is provided an axially adjustable spring-loaded spindle projecting beyond the ends thereof, the end of which facing the base plate is connected with a gripping part of the clamping head which cooperates via a wedge body with a radially expandable gripping sleeve surrounding it concentrically which sleeve, with an outer sleeve, bounds a ring-shaped gripping slot with an insertion opening for the end of the tube body. For use in the case of tube bodies of circular cross-section, the boundary surfaces of the gripping sleeve and of the outer sleeve are circularly cylindrical on the gripping slot. The edge of the tube covering impinges against a radial shoulder on the upper end of the gripping slot so that no counter displacement takes place during the compressing procedure. In the case of pressing down of the spindle, the gripping sleeve is disengaged from the wedge body of the gripping part so that the gripping slot has a maximum width and permits a simple insertion of the open end of the tube body. In the case of upward movement of the spindle, it takes the gripping part with it which now widens out radially the gripping collar over the wedge body, whereby the clamping slot narrows and the open end of the tube body is gripped. The gripping force of the gripping slot is so strong that it prevents a detachment of the tube body from the clamping head during the pulling out procedure.

According to the present invention, it is provided that the gripping part and the gripping sleeve have, in the region of the gripping slot, tapered rings with complementary wedge surfaces inserted into one another which diverge towards the insertion opening of the gripping slot and that the gripping sleeve is provided in its circumferential wall with several open-ended longitudinal slots. The gripping sleeve is cylindrical and is divided by the longitudinal slots in arcuate sections which make possible a radial expansion or contraction thereof in the region of the gripping slot.

The gripping part is screwed to a threaded end of the spindle and secured against rotation in the clamping sleeve by groove-spring fitting. The groove-spring fitting is preferably provided in the region of the complementary wedge surfaces.

The outer edge of the gripping sleeve and the inner edge of the outer sleeve are counter-rounded on the insertion opening of the gripping slot. In this way, a bell-like widening results on the insertion opening which simplifies the insertion of the open tube body. The outer circumference of the gripping sleeve is, in the region of the gripping slot, so adapted to the diameter of the tube body that this sits firmly on the gripping sleeve and does not form any creases or undulations in this region.

BRIEF DESCRIPTION OF THE DRAWINGS

FIG. 4 is a partially cut-away view of the gripping sleeve belonging to the clamping head;

FIG. 5 is a lower view of the gripping sleeve according to FIG. 4 and

FIG. 6 is a partial section of the gripping part before the assembly of an anti-twist element.

DETAILED DESCRIPTION OF THE PREFERRED EMBODIMENT

Figure 1:
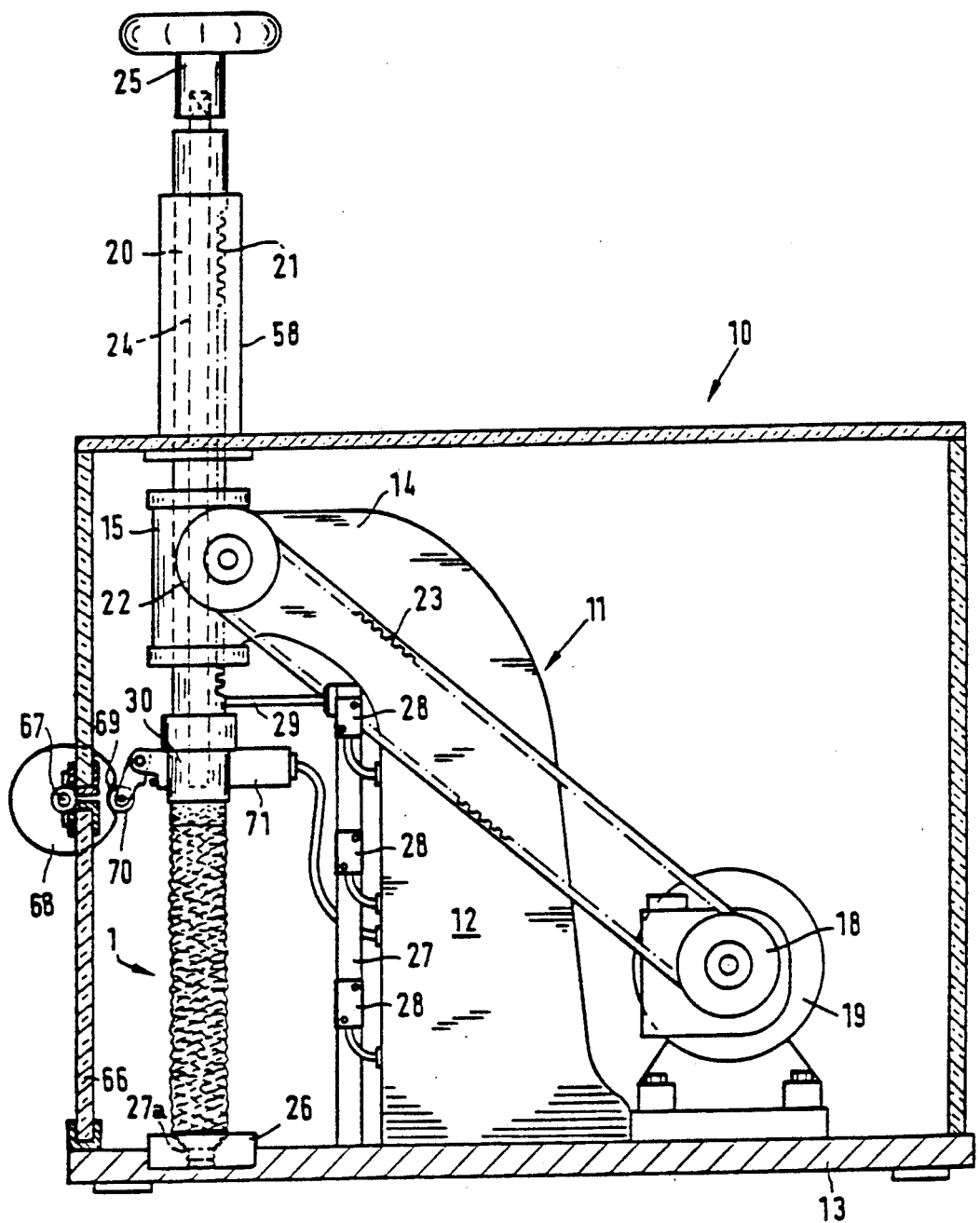
FIG. 1 is a side view of the test device at the end of the pulling out procedure.

The test device 10 for the determination of the strength of adhesion of a protective lacquering on a tube body 1 comprises a J-shaped yoke stanchion 11, the column 12 of which is mounted on a base 13 and the approximately horizontal upper arm 14 of which has, on the free end thereof, a vertical bearing bush 15 for guiding a straight rod 20, which rod 20 serves as a compression means. It has an essentially circular cross-section and, on one side, is provided with a longitudinally-running toothed rod profiling 21. The toothed rod profiling 21 engages with a toothed driving element which is housed in a second bearing bush 16 of the arm 14 running transversely to the bearing bush 15. A drive shaft 22 of the driving element protrudes outwardly on one end over the second bearing bush 16 and is looped round on a pulley 17 by an endless toothed belt 23, the other deflection position of which engages on a pulley 18 on the shaft of an electromotor 19. The electromotor 19 is, viewed from the front of the test device 10, firmly screwed behind the column of the yoke stanchion 11 on the base 13. On the front side of the column 12 is mounted a vertical bar 27 on which are fixed three limit switches 28 with which a contact member 29 projecting from the rod 20 cooperates in order to define the path of compression depending upon the length of the tube body 1 to be tested. Rod 20 is also guided by a vertical bearing 58 fixed to casing 65.

For reasons of safety, the test device 10 is housed in a casing 65 which is closed on all sides and preferably consists of a transparent plastic material. The handling region of the test device is accessible through a casing opening which can be opened and closed by a swingable flap 66 mounted on an upper horizontal axis 67. On one end, the swingable flap 66 is connected with a circular disc 68 with a pitch circular notch 69 which, when the swingable flap 66 is closed, is inwardly directed and engages a roll 70 of a motor safety switch 71. The roll 70 is present on a tiltable lever which, when the swingable flap 66 is open, is pressed by the circumference of the disc 68 against a switch-off knob of the motor safety switch 71 so that, when the swingable flap 66 is open, the motor does not run. When the swingable flap 66 is closed, the electro-motor 19 is switched on in the desired manner by means of an electrical control means provided outside of the casing 65.

Figure 3:
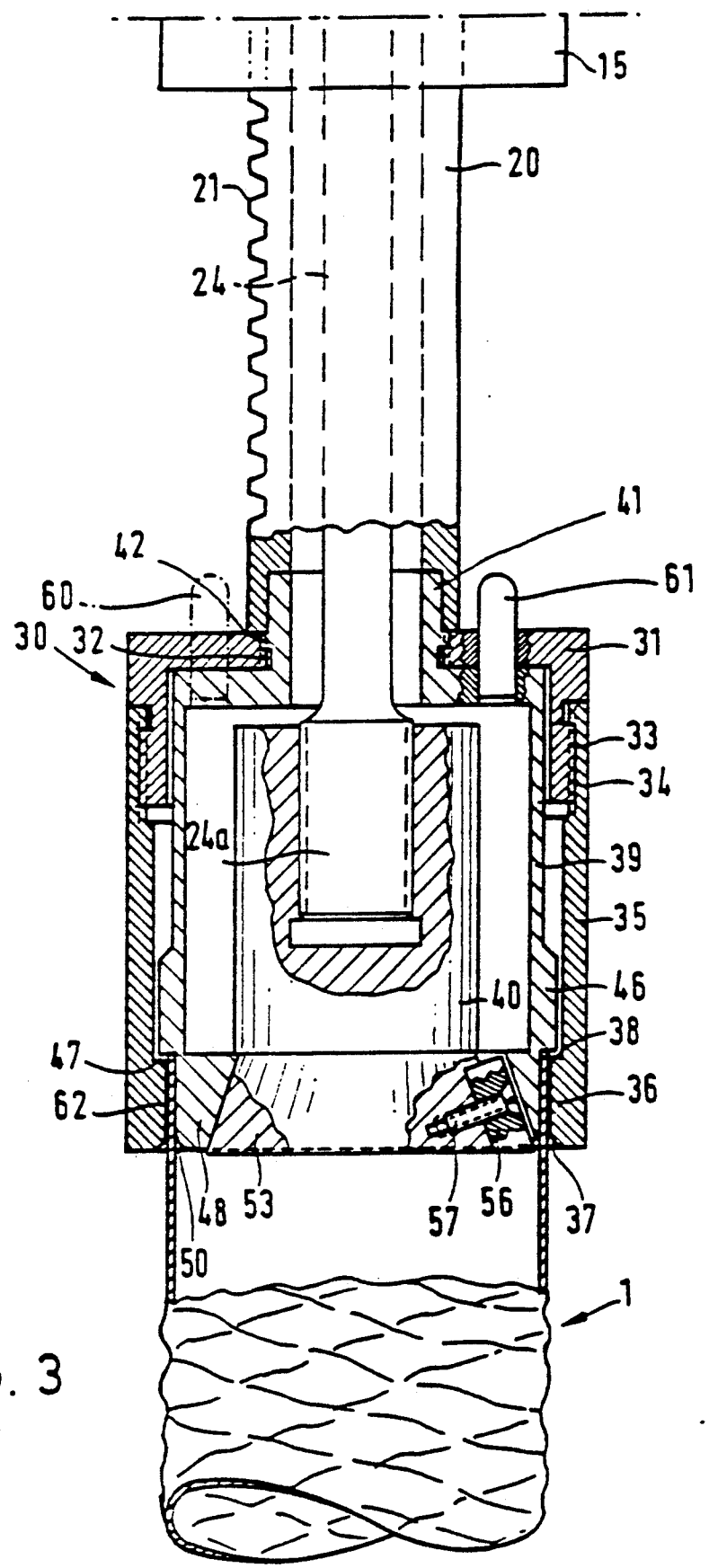
FIG. 3 is a longitudinal section through the clamping head.

The rod 20 is hollow and contains a straight spindle 24 (see FIG. 3), the upper end of which carries a somewhat protruding polyhedron on which can removably be placed a hand grip 25. The lower end of the spindle 24 has a threaded section 24a which projects beyond the lower end of the rod 20. By rotation of the hand grip 25, the spindle 24 is moved upwardly or downwardly and thereby results in the gripping part being opened or closed.

The purpose of this function is explained in more detail in connection with the illustration of a clamping head 30 according to FIGS. 3 to 6 connected with the spindle 24.

On the base 13, vertically under the rod 20, is fixed a base plate 26 which has a central, funnel-shaped recess 27a in the tip of which is formed an internally threaded bore. Against the circular-conically shaped wall of the funnel-shaped recess 27a lies the sloping shoulder of the tube body 1 when the tube thread is screwed into the internally threaded bore. In order to achieve this, the rod 20 is raised and the tube body 1, which is circular cylindrical in the illustrated example, projects upwardly so that its upper circular opening lies centered opposite the clamping head 30 of the test device 10.

The clamping head 30 consists of several substantially circular cylindrical parts which are assembled coaxially. All the component parts are made from high-quality steel. A circular cylindrical cap 31 is provided in its upper plate with a central opening 32 and its comparatively short mantel has an external thread 33 on the free end. The external thread 33 of the cap 31 is screwed on to a circular cylindrical outer sleeve 35 by means of an internal thread 34 on the free end of this sleeve 35. The outer circumferences of these two parts run flush. On the lower edge of the outer sleeve 35 is formed a surrounding inner collar 36 with circular cylindrical inner surface, the lower inner edge 37 of which is rounded, whereas its upper flank 38 runs at right-angles. Before screwing together the parts 31 and 35, in the outer sleeve 35 is placed a gripping sleeve 39 which contains a gripping part 40.

The gripping sleeve 39 is to be seen in FIGS. 4 and 5. It also has a circular cylindrical beaker shape and its upper end fits into the cap 31, whereby it projects outwardly with a hollow pipe 41 formed on its plate through the central opening 32 and an outer ring collar 42 of the hollow pipe 41 is screwed, for example, into the opening 32. Three parallel edged longitudinal slots 43, each of which starts from a hole 44 in the upper half of the wall of the gripping sleeve 39, end openly on the lower edge of the gripping sleeve 39 and divide it into three arcuate segments 45 which can be radially deflected so that the gripping collar 39 can be widened in its lower region. The lower edge region of the gripping sleeve 39 forms a tapered ring 48 with circular cylindrical outer surface and downwardly diverging circular inner wedge surface 49. On one point of the wedge surface 49 is formed a longitudinally running groove 51 which extends over the total height of the tapered ring 48. The outer edge 50 of the gripping sleeve 39 is rounded counter to the inner edge 37 of the outer sleeve 35. Between the circular cylindrical outer circumference of the tapered ring 48 and the circular cylindrical inner circumference of the inner collar 36 of the outer sleeve 35, there remains a gripping slot 62 for the reception of the upper open end of the tube body 1. On the inner end of the gripping slot 62, the gripping sleeve 39 is provided, at a distance from its lower open edge, with an outer ring bead 46, the lower flank 47 of which projects next to the upper flank 38 of the inner collar 36 of the outer sleeve 35 at right-angles to the circular cylindrical mantel surface.

The main component of the clamping head 30 is the gripping part 40 which consists, in one piece, of a circular cylindrical shaft 52 and a tapered ring 53 formed on one end, the outer wedge surface 54 of which diverges downwardly and the inclination of which and the axial length of the wedge surface 49 are adapted to the gripping sleeve 39. In the shaft 52 is present a coaxial inner threaded bore 55 which is closed below and open above. It serves for the screw connection of the gripping part 40 with the threaded end 24a of the spindle 24. The gripping part 40 is axially movable in the gripping sleeve 39 but is made non-rotatable. As a protection against thread stripping, there serves the groove 51 in the tapered ring 48 in which is inserted a fitting piece 56 which is fixed by means of a screw 57 and projects with about half of its thickness region over the wedge surface 54 so that there is obtained a groove-spring fit as protection against thread stripping.

Figure 2:
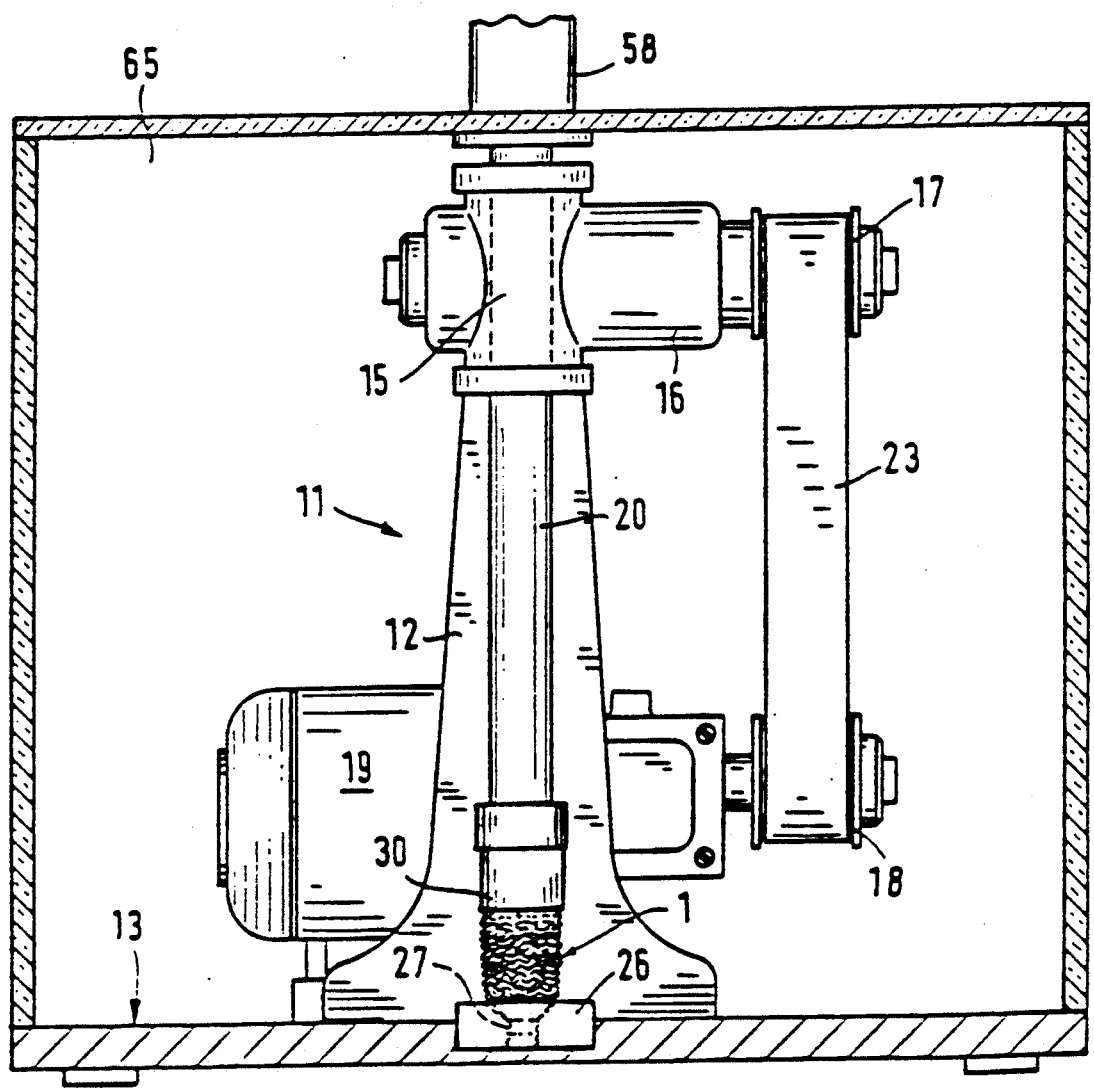
FIG. 2 is a front view of the test device at the end of the compressing procedure.

For the assembly of the clamping head 30, the gripping sleeve 39 is placed in the outer sleeve 35 and the gripping part 40 is introduced from below into the gripping sleeve 39 until the tapered rings 48 and 53 engage into one another. The cap 31 is then screwed with the outer sleeve 35 so that there is obtained a cylindrical body closed on all sides which is fixed to the rod 20 by screwing of the gripping part 40 with the spindle 24. In the case of the fully assembled clamping head 30, which is centered by two centering pins 60 and 61 in the plate parts of the cap 31 lying next to one another and the gripping sleeve 39, the gripping slot 62 has a certain breadth which can be altered. For the reception of the edge of the tube body 1 or for the release thereof, by screwing down of the spindle 24, the tapered ring 53 of the gripping part 40 is somewhat pressed out downwardly from the tapered ring 48 so that this assumes its relaxed basic position in which the gripping slot 62 has its maximum breadth. The leading edge of the edge of the tube 1 is pushed against the lower flank 47 of the ring bead 46 of the gripping sleeve 39 so that no displacement can take place in the case of downward movement of the rod 20 for the compression of the tube body 1. When, by screwing up of the spindle 24, the tapered ring 53 is drawn into the tapered ring 48, the cooperation of the wedge surfaces 49 and 54 radially spreads out somewhat the gripping sleeve 39, especially in the region of the tapered ring 48, and the edge of the tube 1 is firmly clamped in the gripping slot 62. By lowering the rod 20, the tube body 1 is compressed exactly in a straight line (see FIG. 2). The speed of compression is thereby preferably 157 mm/s. For opening out the compressed tube, the rod 20 is moved upwardly with the same speed so that the tube body 1, firmly held at both ends, is pulled out (see FIG. 1). Subsequently, by release of the gripping action of the clamping head 30, the upper end of the tube body 1 is freed and the thread neck of the tube can then be screwed out from the base plate 26. For examination purposes, the tube body 1 is cut up longitudinally and inspected.

We claim:

1. Test device for the determination of the strength of adhesion of a protective lacquering on the body of a collapsable tube, said device comprising a base plate with a recessed seating for the shoulder of a tube with a threaded neck and a compressing means engaging the open end of the tube body, said compressing means being mounted axially with respect to said tube, wherein the compressing means comprises a reciprocable rod (20) which, on the end thereof facing the base plate (26), has a clamping head (30) for clamping the open end of the tube body and, in a conical recess in the base plate (26), there is provided an internally threaded bore for screwing in the threaded neck of the tube (1).

2. Test device according to claim 1, wherein the compressing means is adapted to compress the tube body (1) at a predetermined uniform rate and subsequently to pull it out again at the same predetermined uniform rate.

3. Test device according to claim 1, wherein the rod (20) is mounted in a guide (15) of a yoke stanchion (11) and is driven via an external toothed rod member (21) coupled with an electromotor (19), the rod (20) having a contact member (29) which cooperates with limit switches (28) arranged according to height.

4. Test device according to claim 3, wherein the yoke stanchion (11) and the electromotor (19) are housed in a casing (65) made of transparent material which, in the region of the base plate (26) and clamping head (30), has an opening closed by a swingable flap (66), the swingable flap (66) activating motor safety switch (71) via an operating element (68).

5. Test device according to claim 1 wherein, the rod (20), has an axial bore and an axially adjustable spindle (24) projecting beyond both ends of said bore, the end of said spindle facing the base plate (26) being connected with a gripping part (40) of the clamping head (30) which cooperates via a wedged body with a radially expandable gripping sleeve (39) surrounding said gripping part concentrically, which gripping sleeve, with an outer sleeve (35), bounds a ring-shaped gripping slot (62) with an insertion opening for the end of the tube body.

6. Test device according to claim 5, wherein the gripping part (40) and the gripping sleeve (39) have, in the region of the gripping slot (62), tapered rings (53;48) engaging into one another with complementary wedge surfaces (54;49) which diverge against the insertion opening of the gripping slot (62), the gripping sleeve (39) being provided on its circumferential wall with several open-ended longitudinal slots (43).

7. Test device according to claim 5, wherein the gripping part (40) is screwed to a threaded end (24a) of the spindle (24) and is secured against rotation in the gripping sleeve (39) by groove-spring fitting (51,56).

8. Test device according to claim 5, wherein the outer edge (50) of the gripping sleeve (39) and the inner edge (37) of the outer sleeve (35) are counter rounded on the insertion opening of the gripping slot (62).

9. Test device according to claim 3 further comprising a casing (65) externally of the base plate (26), the clamping head (30), and the electromotor (19), wherein the electromotor (19) is controllable by an electrical control device provided outside of the casing (65).

* * * * *